United States Patent
Tuerk et al.

(10) Patent No.: US 10,428,447 B2
(45) Date of Patent: Oct. 1, 2019

(54) COMPRESSION DEVICE

(71) Applicant: BSN-JOBST GmbH, Emmerich (DE)

(72) Inventors: Alexander Tuerk, Wuppertal (DE);
Marius Chrost, Wuppertal (DE);
Joachim Bauer, Hamburg (DE);
Juergen Greve, Emmerich (DE)

(73) Assignee: BSN-JOBST GmbH, Emmerich (DE)

( * ) Notice: Subject to any disclaimer, the term of this patent is extended or adjusted under 35 U.S.C. 154(b) by 58 days.

(21) Appl. No.: 15/571,584

(22) PCT Filed: May 4, 2016

(86) PCT No.: PCT/EP2016/060085
§ 371 (c)(1),
(2) Date: Nov. 3, 2017

(87) PCT Pub. No.: WO2016/177829
PCT Pub. Date: Nov. 10, 2016

(65) Prior Publication Data
US 2018/0153224 A1    Jun. 7, 2018

(30) Foreign Application Priority Data
May 4, 2015 (DE) .......... 10 2015 106 903

(51) Int. Cl.
*D04B 1/26* (2006.01)
*D04B 9/52* (2006.01)
*A61F 13/08* (2006.01)
*A41B 11/12* (2006.01)

(52) U.S. Cl.
CPC ............ *D04B 1/265* (2013.01); *A41B 11/126* (2013.01); *A61F 13/08* (2013.01); *D04B 9/52* (2013.01)

(58) Field of Classification Search
CPC ..... A41B 11/126; A41B 11/128; A61F 13/08; D04B 1/265; D04B 9/52
See application file for complete search history.

(56) References Cited

U.S. PATENT DOCUMENTS

| 2,169,203 | A | * | 8/1939 | Hinchliff | D04B 1/26 602/62 |
| 2,977,782 | A | * | 4/1961 | Sheek | A41B 11/12 2/9 |
| 3,359,571 | A | * | 12/1967 | Burke | A41F 11/18 2/240 |

(Continued)

FOREIGN PATENT DOCUMENTS

| DE | 82 17 651 U1 | 9/1982 |
| FR | 1 519 361 A | 3/1968 |

OTHER PUBLICATIONS

International Search Report of PCT/EP2016/060085, dated Aug. 31, 2016.

(Continued)

*Primary Examiner* — Danny Worrell
(74) *Attorney, Agent, or Firm* — Collard & Roe, P.C.

(57) ABSTRACT

A compression article which is produced from an elastic textile material, in particular a knitted fabric, and which is provided with at least one elastic holding strap which protects against slipping on the body part, characterized in that the holding strap is produced using a friction thread which is located in places on the strap inner side on the surface of the strap.

10 Claims, 1 Drawing Sheet

(56) References Cited

U.S. PATENT DOCUMENTS

| | | | |
|---|---|---|---|
| 3,386,270 A | 6/1968 | Simmons | |
| 3,389,722 A * | 6/1968 | Howard | D03D 15/08 139/423 |
| 3,729,956 A * | 5/1973 | Nebel | A41B 11/04 66/172 E |
| 3,800,331 A | 4/1974 | Taddeo | |
| 3,908,407 A * | 9/1975 | Brand | D04B 1/106 66/172 E |
| 3,975,929 A * | 8/1976 | Fregeolle | D04B 1/106 602/63 |
| 3,983,870 A * | 10/1976 | Herbert | A41B 11/12 602/63 |
| 5,497,513 A * | 3/1996 | Arabeyre | A61F 13/08 2/16 |
| 5,540,063 A * | 7/1996 | Ferrell | D04B 1/106 66/172 E |
| 2003/0213269 A1* | 11/2003 | Peeler | A61F 13/08 66/171 |
| 2012/0324961 A1 | 12/2012 | Clemendot | |

OTHER PUBLICATIONS

ASTM Standard D 3108-01, Standard Test Method for Coefficient of Friction, Yarn to Solid Material, Sep. 2001, pp. 1-6.

* cited by examiner

COMPRESSION DEVICE

CROSS REFERENCE TO RELATED APPLICATIONS

This application is the National Stage of PCT/EP2016/060085 filed on May 4, 2016, which claims priority under 35 U.S.C. § 119 of German Application No. 10 2015 106 903.2 filed on May 4, 2015, the disclosures of which are incorporated by reference. The international application under PCT article 21(2) was not published in English.

BACKGROUND OF THE INVENTION

The invention relates to a compression article which is produced from an elastic textile material, in particular a knitted fabric, and is provided with at least one elastic holding strap to protect against slipping on the body part.

Such compression articles are already known, in particular, in the form of leg or knee stockings. Thus, for example, the utility model DE 82 17 651 U1 describes a medical rubber stocking with a holding strap, which is configured as a crochet galloon strap and is provided on its inside with a plurality of nubs made of silicone.

The nubs on the inner side of the holding strap reliably prevent the stocking from slipping, but at the same time restrict the respiratory activity of the skin. The nubs or strips of the known holding straps have a relatively large surface in this case and are always located on the same skin areas in medical compression articles which are to be worn every day for up to sixteen hours. Skin irritations can therefore occur which limit the wearing comfort of the articles.

Moreover, the production of the known holding straps by the subsequent application of the silicone nubs or strips is relatively complicated and cost-intensive.

SUMMARY OF THE INVENTION

The present invention is therefore based on the object of proposing a compression article which avoids the disadvantages mentioned.

The object is achieved by a compression article having the features of patent claim 1. The elastic knit, knitted fabric or fabric can be anatomically adapted in shape to the part of the body to be supported. The holding strap may preferably be a woven strap produced using a friction thread which is located in places on the strap inner side on the surface of the strap. Knitted or rustle knitted straps are also conceivable. The friction thread can be completely covered by other threads on the strap outer side.

A subsequent application of silicone nubs or strips is superfluous due to the incorporation of the friction threads into the strap. Moreover, the individual locations at which the friction thread is located on the surface of the holding strap have only very small dimensions so that the respiratory activity of the skin is only slightly affected. The yarn thicknesses used are usually between 15 dtex and 5,000 dtex. The wearing comfort of the compression articles according to the invention is therefore extremely high. However, the holding strap performs a comparable holding function as the holding straps of known compression articles. All yarns with a friction coefficient of more than 0.4 are considered fiction friction threads.

The friction coefficient is determined according to the method described in ASTM Standard D 3108-95 with the following extensions: A device according to FIG. 2 of this standard is used, and the thread to be examined is wound around a ceramic rod at an angle of 163.5°, wherein the rod has a diameter of 8 mm. The initial load with which the thread to be examined is subjected is 3.0 g, independent of the dtex value of the examined thread. The value of the friction coefficient is then calculated from the measured values for the input tension and the output tension as described in the standard.

It has been found that the total area of the locations where the friction thread is present on the surface of the inner side of the strap can be less than 25% of the surface area, preferably less than 15% of the strap inner side without impairing the holding function of the holding strap. This is significantly less silicone surface than with conventional holding straps with applied silicone nubs or strips. Skin irritations occur only slightly on such small surfaces having little respiratory activity.

Preferably, the holding strap can exert a compression pressure that is in a fixed ratio to the compression pressure of the knitted fabric so that the desired compression pressure at the opening margins of the compression article is also ensured. The knitted fabric has a continuous drop in the compression pressure from distal to proximal. The holding strap may continue this pressure drop or may exert a higher pressure than the adjacent knitted fabric to enhance the holding function.

Further advantages are obtained if the locations at which the friction thread is located on the surface of the strap inner side are uniformly distributed over the strap inner side. The holding function is then the same at all locations of the holding strap. In addition, the skin is evenly loaded. Naturally, however, a non-uniform distribution of the locations at which the friction threads is located on the surface of the strap is also possible, if this is necessary, for example, because of particularly sensitive skin zones or the like.

In a preferred variant of the compression article, a part of the warp threads of the holding strap consists of the friction thread. On the outer side of the holding strap, these warp threads can be completely covered and on the inner side partially covered by weft threads of another material.

Spandex, natural rubber, silicone or synthetic rubber are possible friction thread materials. It is also possible to use coated yarns, wherein the coating may consist of vulcanized elastomers, liquid silicone, silicone rubber and/or polyurethane elastomers.

In addition to the friction thread, the holding strap can preferably contain gimped elastic threads and polyamide threads. With the elastic threads, the desired compression pressure can be adjusted while the polyamide threads ensure the required stability of the holding strap.

The friction thread can preferably be transparent or translucent and thus not noticeable optically. It can be easily combined with any color of the other threads.

Furthermore, the holding strap can be sewn onto the knitted fabric in a manner known per se. A weld seam between the knitted fabric and the holding strap is also possible in principle.

BRIEF DESCRIPTION OF THE DRAWINGS

The drawing shows a possible exemplary embodiment of a compression article according to the invention.

It shows.

DETAILED DESCRIPTION OF THE INVENTION

Figure 1:
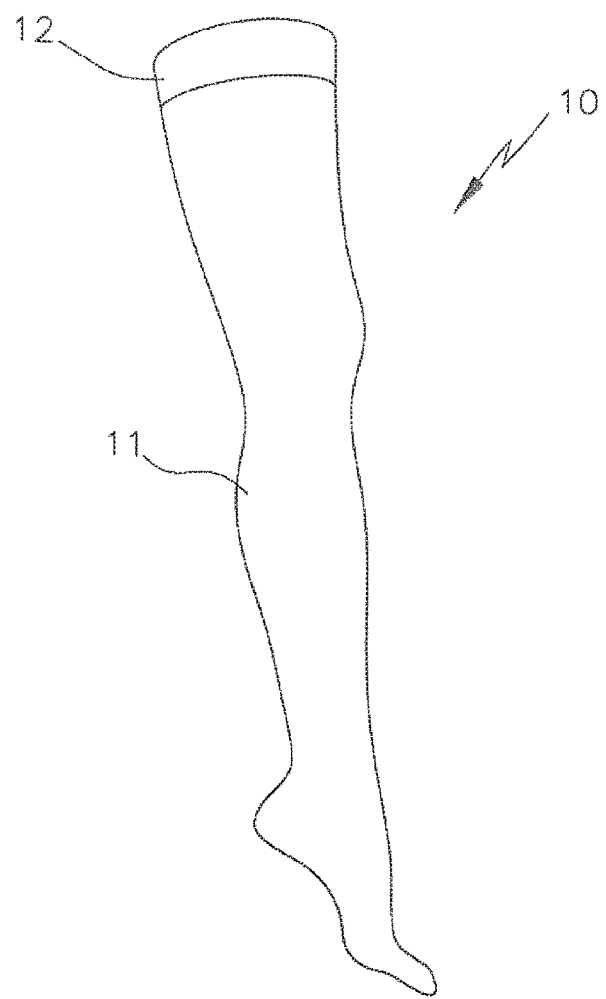
FIG. 1 a schematic representation of a compression stocking with a holding strap.

The compression stocking 10 of FIG. 1 is a leg stocking extending up to the thigh of the wearer. It consists of a knitted fabric 11 adapted to the anatomical shape of the leg, on the upper edge of which a holding strap 12 is sewn. The holding strap 12 secures the stocking 10 against slipping.

Figure 2:
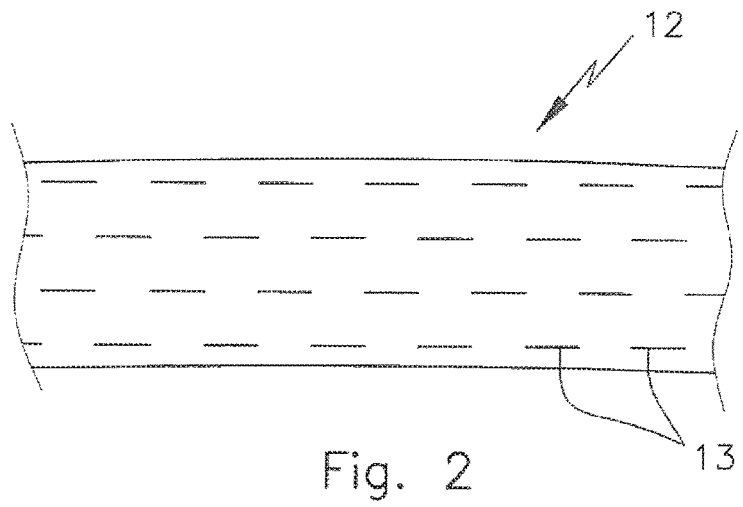
FIG. 2 a detail view of the inner side of the holding strap from FIG. 1.

As shown in the detailed view of the inner side of the strap 12 of FIG. 2, the holding strap 12 is a woven strap produced using a friction thread 13 which is located on the surface of the strap inner side uniformly distributed over the surface of the inner side of the strap and thus comes into contact with the skin of the wearer of the compression article 10. The friction thread 13 thus ensures the holding function of the holding strap 12. In this case, it virtually does not restrict the respiratory activity of the holding strap 12, so that the compression stocking has a high wearing comfort.

What is claimed is:

1. A compression article for supporting a body part, said compression article being produced from an elastic textile material, in the form of a knitted fabric (11), and which is provided with at least one elastic holding strap (12) which protects against slipping on the body part, wherein the holding strap (12) is produced using a friction thread (13) which is located in places on a surface of the strap (12) on an inner side of the strap, wherein the total area of the locations at which the friction thread (13) is located on the surface of the inner side of the strap is less than 25% of the surface of the inner side of the strap.

2. The compression article according to claim 1, wherein the holding strap (12) is a woven strap.

3. The compression article according to claim 1, wherein the friction thread (13) is completely covered by other threads on an outer side of the strap.

4. The compression article according to claim 1, wherein the holding strap (12) exerts a compression pressure which is in a fixed ratio to a compression pressure of an adjacent region of the knitted fabric (11), so that the holding strap (12) continues the continuous drop in the compression pressure from a distal end to a proximal end of the knitted fabric (11), or exerts a higher pressure than the adjacent knitted fabric (11).

5. The compression article according to claim 1, wherein the knitted fabric (11) is adapted anatomically to the body part to be supported.

6. The compression article according to claim 1, wherein the locations at which the friction thread (13) is located on the surface of the strap inner side are uniformly distributed over the inner side of the strap.

7. The compression article according to claim 2, wherein the friction thread forms a part of the warp threads of the holding strap (12).

8. The compression article according to claim 1, wherein the holding strap (12) also comprises gimped elastic threads and polyamide threads.

9. The compression article according to claim 1, wherein the friction thread (13) is transparent or translucent.

10. The compression article according to claim 1, wherein the holding strap (12) is sewn onto the knitted fabric (11).

\* \* \* \* \*